(12) United States Patent
Richard

(10) Patent No.: US 9,579,169 B2
(45) Date of Patent: Feb. 28, 2017

(54) DENTAL PROSTHETIC ASSEMBLY COMPRISING A DENTAL IMPLANT AND A TRANSFIXED DENTAL PROSTHESIS

(71) Applicant: ANTHOGYR, Sallanches (FR)

(72) Inventor: Hervé Richard, Notre Dame de Bellecombe (FR)

(73) Assignee: ANTHOGYR, Sallanches (FR)

( * ) Notice: Subject to any disclaimer, the term of this patent is extended or adjusted under 35 U.S.C. 154(b) by 286 days.

(21) Appl. No.: 14/515,049

(22) Filed: Oct. 15, 2014

(65) Prior Publication Data
US 2015/0118651 A1 Apr. 30, 2015

(30) Foreign Application Priority Data
Oct. 25, 2013 (FR) ...................... 13 60411

(51) Int. Cl.
*A61C 8/00* (2006.01)
*A61C 13/265* (2006.01)

(52) U.S. Cl.
CPC ............. *A61C 8/0062* (2013.01); *A61C 8/005* (2013.01); *A61C 8/006* (2013.01); *A61C 8/0048* (2013.01); *A61C 8/0056* (2013.01); *A61C 8/0075* (2013.01); *A61C 8/0095* (2013.01); *A61C 13/2656* (2013.01)

(58) Field of Classification Search
CPC ....... A61C 8/005; A61C 8/006; A61C 8/0062; A61C 8/0095; A61C 8/0048; A61C 8/0056; A61C 8/0075; A61C 13/2656
See application file for complete search history.

(56) References Cited

U.S. PATENT DOCUMENTS

| 6,663,389 B1 * | 12/2003 | Gallicchio | A61C 8/005 433/173 |
| 6,846,180 B1 * | 1/2005 | Joos | A61C 8/0022 433/174 |
| 8,992,221 B2 * | 3/2015 | Bolleter | A61C 8/005 433/173 |
| 9,039,415 B2 * | 5/2015 | Streff | A61C 8/0048 433/173 |
| 2008/0286721 A1 | 11/2008 | Walther | |
| 2013/0164708 A1 | 6/2013 | Streff | |

FOREIGN PATENT DOCUMENTS

| EP | 0867154 A1 | 9/1998 |
| EP | 1992304 B1 | 11/2008 |
| EP | 2607722 A1 | 6/2013 |

* cited by examiner

*Primary Examiner* — Glenn Richman
(74) *Attorney, Agent, or Firm* — William H. Eilberg

(57) ABSTRACT

Dental prosthetic assembly (27) comprising a dental implant (2a, 2b) and a transfixed dental prosthesis (3). A connecting device (1) comprises:
- a lock (5) which has at least two radial wings (6a) and is mounted rotatably and retained in translation in one of dental implant (2a, 2b) or dental prosthesis (3),
- a retention cavity (15), provided on its periphery with protuberances (16a) extending radially towards the centre of the retention cavity (15), which is formed in the other of dental implant (2a, 2b) or dental prosthesis (3).

The radial wings (6a) and the protuberances (16a) are configured and dimensioned in such a way as to cooperate by rotation of the lock (5) in order to keep the dental prosthesis (3) transfixed on the dental implant (2a, 2b), and in such a way as to allow the lock (5) and its radial wings (6a) to penetrate into the retention cavity (15) by a simple movement of axial translation.

11 Claims, 10 Drawing Sheets

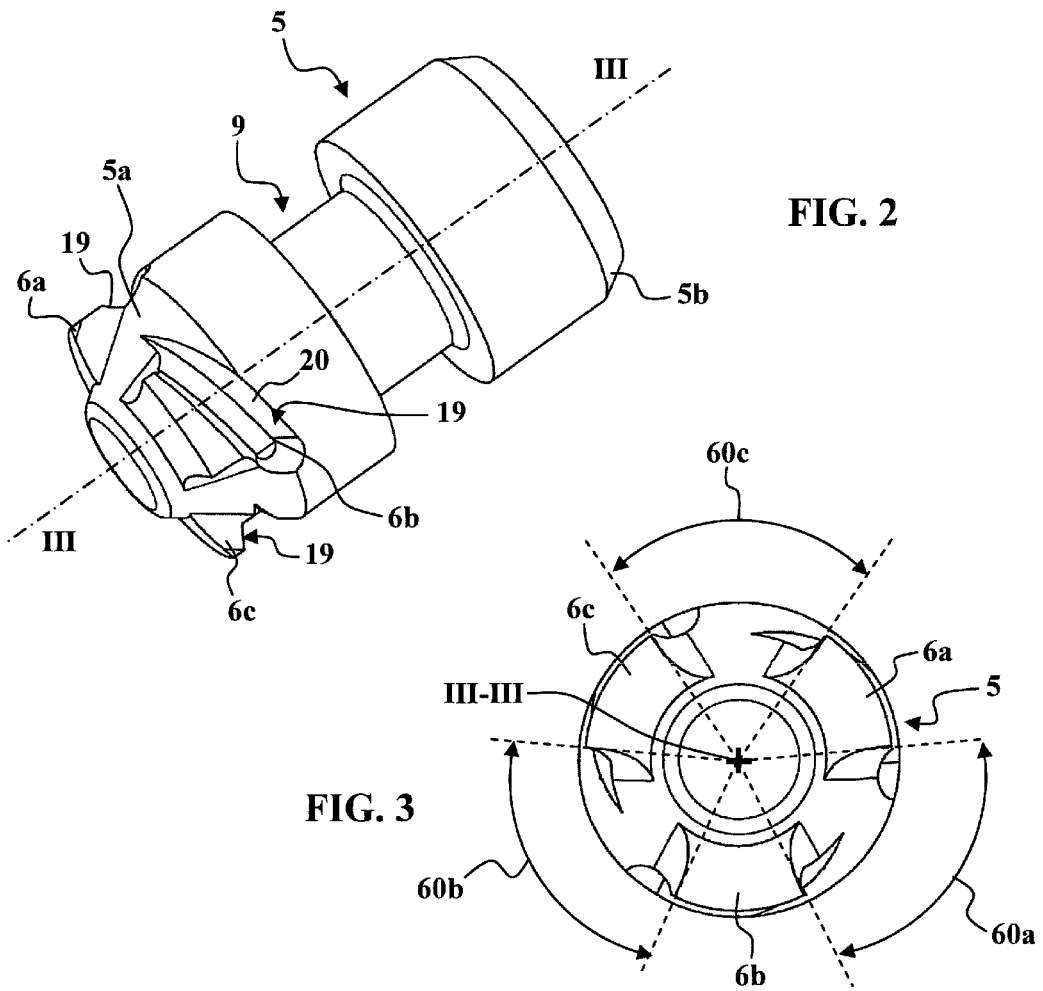
FIG. 2
FIG. 3
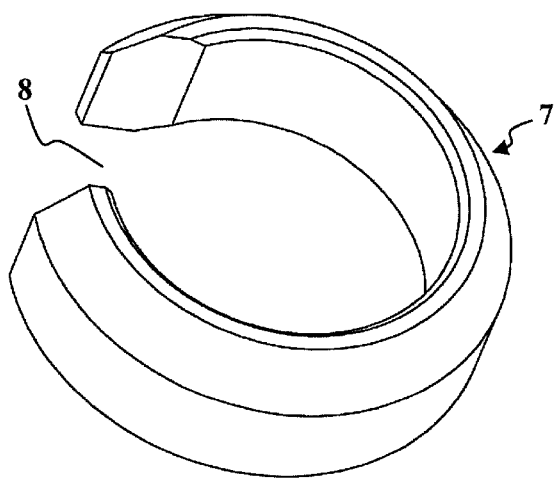
FIG. 4

US 9,579,169 B2

DENTAL PROSTHETIC ASSEMBLY COMPRISING A DENTAL IMPLANT AND A TRANSFIXED DENTAL PROSTHESIS

TECHNICAL FIELD OF THE INVENTION

The present invention relates to the field of dental implantology, in particular to treatment of edentulism of the dental arches using a dental prosthetic assembly comprising an implant-supported prosthesis (or possibly several such prostheses) of the type transfixed on at least one dental implant.

An implant-supported prosthesis of the transfixed type is intended to rest on the dental arch of the patient by being fixed to one or more dental implants that are fixed in the jawbone of the patient, so as to form one or more prosthetic teeth. In order to permit possible subsequent removal of the prosthesis, for example for repair, the prosthesis is fixed to the implants by way of fixation means (screws in the prior art) that pass through the prosthesis, hence the expression "transfixed prosthesis". The head of the screws is accessible from the active surface of the prosthesis (or mastication surface).

For reasons of mechanical stability of the implant in the jawbone of the patient in particular, the implants are oriented in axial directions which are oblique with respect to each other and/or oblique with respect to the general surface of the dental arch.

It is known for the implant-supported prosthesis to be fixed to the implants using transfixation screws. On account of the oblique orientations of the implants relative to each other, angled posts are often used. An angled post is an intermediate component intended to be attached to the implant in a first axial direction (corresponding to the longitudinal direction of the implant) and having an internally threaded cavity oriented in a second axial direction forming an angle with the first axial direction. The internally threaded cavity receives the transfixation screw in the second axial direction.

To insert and screw a transfixation screw into an angled post, the prosthesis is provided with an access channel for a rotation drive tool. The access channel is oriented in a third axial direction. The orientation of this access channel must be chosen with care in order to ensure that it does not open out at the top of a prosthetic tooth on the outer active surface of the prosthesis, so as not to adversely affect the strength of the prosthetic tooth in an area that is intended to withstand the forces of mastication. To better meet these needs, the dental practitioner has at his disposal numerous intermediate posts of different sizes and angles. However, an optimal orientation between the first, second and third axial directions is not always possible despite the availability of a large number of different intermediate posts.

It is therefore desirable to propose a solution for removable fixation which permits an optimal orientation of the access channel, taking into consideration the orientation of the implant, and which allows this to be done without having to use too many components that need to be maneuvered and kept in stock by the practitioner.

To achieve this aim, the applicant has envisaged securing the transfixation screws (for example by crimping) of the prosthesis, the transfixation screws then being intended to be screwed directly into the implants.

However, to ensure that a transfixed prosthesis is fitted correctly in the mouth, and to ensure that the practitioner can check its suitability before fixing it, more particularly in the case of an implant-supported multiple prosthesis, it is necessary to begin with a step which involves positioning the prosthesis on the dental arch of the patient. In the solution of crimping captive screws as envisaged by the applicant, this requires that the screws can be received almost completely in the prosthesis. However, the necessary length of the screws makes this impossible in most cases. Even if this were possible, the screw head is then unreachable to be maneuvered by a rotation drive tool inserted via the access channel, on account of the inclination between the first and third directions.

The document EP 1 992 304 A1 does not describe a transfixed dental prosthesis. It describes a dental prosthesis of another type, mounted with a conical fit on a post. The post is therefore not mounted rotatably and retained in translation in the dental prosthesis. The post is itself received with a conical fit in the blind hole of an implant screwed into the jaw of the patient. To oppose axial extraction of the post from the implant, radial wings are provided on the post and, after a slight rotation, are intended to cooperate, by virtue of a matching shape, with wings provided at the mouth of the blind hole of the implant. The wings of the post do not constitute a means for locking the prosthesis on the implant: indeed, the post is fixed in the implant by its wings and a slight rotation even before the post receives the dental prosthesis with a conical fit.

SUMMARY OF THE INVENTION

A problem addressed by the present invention is to allow optimal and removable fixation of an implant-supported prosthesis of the transfixed type, with the aid of connecting means which have a smaller number of constituent elements and which allow a freer choice of orientation of the access channel in the prosthesis.

To achieve these aims, and others, the invention proposes a dental prosthetic assembly comprising:
  a dental implant,
  a dental prosthesis,
  a connecting device comprising a retention cavity, which is formed in one of dental implant or dental prosthesis and which is provided on its periphery with protuberances extending radially towards the centre of the retention cavity;
  according to the invention:
  the dental prosthesis is of the transfixed type,
  the connecting device comprises a lock which has at least two radial wings and is mounted rotatably and retained in translation in the other of dental implant or dental prosthesis, the radial wings and the protuberances being configured and dimensioned in such a way as to allow the lock and its radial wings to penetrate into the retention cavity by a simple movement of axial translation,
  the radial wings and the protuberances are configured and dimensioned in such a way as to cooperate by rotation of the lock in order to keep the dental prosthesis transfixed on the dental implant.

The lock mounted in the dental prosthesis or in the dental implant by way of a pivot connection (or sliding pivot) is directly oriented in a direction intended to be coaxial to the axial direction of the implant, which avoids the need to use angled posts.

The connecting device according to the invention can have a very limited axial extent, since the wings can have a small size in the axial direction of the lock. Moreover, its engagement by a simple movement of axial translation and the configuration of the radial wings and protuberances facilitate the phase of positioning of the prosthesis on the dental arch. To be retained in the retention cavity, the lock only needs to be driven in rotation by less than one complete turn. The maneuvering of the lock is therefore quick and simple. The axial travel needed to manoeuvre the lock and to cause it to be retained in the retention cavity is thus greatly reduced.

Preferably, provision is made that:

the radial wings of the lock are separated from each other by angular sectors which are dimensioned in such a way as to allow a protuberance to pass through by a simple movement of axial translation, the protuberances of the retention cavity are separated from each other by angular sectors which are dimensioned in such a way as to allow a radial wing to pass through during said simple movement of axial translation.

Advantageously, the radial wings of the lock can be carried by a first end portion, which is substantially conical or frustoconical. The substantially conical or frustoconical first end portion permits progressive guidance of the lock in order to centre the latter with respect to the retention cavity. The expression "substantially frustoconical end portion" is understood as designating any geometrical shape that narrows gradually and can, for example, be a rounded end.

Preferably, the lock can have a socket allowing it to be driven in rotation with the aid of a tool. This socket can be situated at an end of the lock opposite the end carrying the radial wings.

Advantageously, the radial wings can have a bearing facet with a progressive incline intended to bear against a protuberance of the retention cavity, and/or the protuberances can have a retention facet with a progressive incline intended to bear against a radial wing of the lock.

The incline(s) of the bearing facets and/or retention facets allow the prosthesis to be guided radially and driven in translation with respect to the implant during the manoeuvre of rotation of the lock, and they ensure excellent pressing of the prosthesis on the implant.

In a first embodiment according to the invention, the lock can be mounted rotatably and retained in translation in the dental prosthesis by way of a compressible retention ring, preferably by means of a slit, engaging simultaneously in an outer peripheral groove formed on the lock and in an inner peripheral groove formed in the dental prosthesis.

The lock is thus arranged as a pivot joint (or sliding pivot) in the prosthesis and is held captive in the prosthesis in a simple and effective way.

To ensure the connection between the prosthesis and the implant, the practitioner introduces a rotation drive tool into the access channel formed in the prosthesis until the tool is engaged on the lock, in order to push the latter into the retention cavity of the implant and then to drive it in rotation.

However, to allow the lock to be disassembled if it is accidentally damaged, the dental prosthesis can advantageously have a plurality of open axial channels extending as far as the inner peripheral groove formed in the dental prosthesis.

A tool for withdrawing the lock can thus be introduced, said tool having a plurality of rods designed to penetrate into the axial channels until they come to bear against the compressible retention ring in order to press the latter radially in a centripetal manner, thereby reducing its radial dimensions, then to extract the retention ring from the dental prosthesis and thereby free the lock.

Preferably, the inner peripheral groove, formed in the dental prosthesis, and/or the outer peripheral groove, formed on the lock, have a height which is slightly greater than that of the retention ring, permitting axial play in translation between the dental prosthesis and the lock.

The axial play in translation, brought about by the difference in height between the retention ring and the inner peripheral groove formed in the prosthesis and/or the outer peripheral groove formed on the lock, allows the ring, and thus the lock, to be easily mounted in the prosthesis. This also allows the lock to retreat a little in the prosthesis in order to be partially or completely received therein when the radial wings of the lock are not strictly aligned with the spaces between the protuberances of the retention cavity during the positioning of the prosthesis on the dental arch. In other words, the lock is arranged as a sliding pivot joint in the prosthesis, with a sliding travel that is determined by the axial play in translation between the dental prosthesis and the lock.

In a second embodiment according to the invention, the lock can be mounted rotatably and retained in translation in the dental implant by way of:

an inner peripheral groove situated in a receiving cavity formed in the dental implant, a second end of the lock having snap-fit means intended to penetrate the inner peripheral groove of the receiving cavity.

To ensure the connection between the prosthesis and the implant, the practitioner engages the prosthesis on the implant and the lock, such that the first end portion of the lock penetrates into the retention cavity of the prosthesis, after which he introduces a rotation drive tool into the access channel formed in the prosthesis and passes it through the retention cavity formed in the prosthesis in order to reach the lock, arranged in the implant, and drive it in rotation.

All the embodiments make it possible to limit the stock of components kept by the practitioners, to simplify the surgical procedure, to limit the size of the constituent elements of the connection between the prosthesis and the one or more implants, and to permit a more flexible choice as regards the orientation of the access channels provided in the prosthesis.

The second embodiment also has the advantage that most of the bulk of the connecting device is at the implant side, whereas the socket situated on the prosthesis has a greatly reduced size. Thus, during production of the prosthesis, the prosthetist is even less constrained in orienting the access channels.

BRIEF DESCRIPTION OF THE DRAWINGS

Other subjects, features and advantages of the present invention will become clear from the following description of particular embodiments, with reference being made to the attached figures in which:

FIG. 2 is a perspective view of a lock used in a connecting device of the first embodiment of a dental prosthetic assembly according to the invention;

FIG. 3 is a bottom view of the lock from FIG. 2;

FIG. 4 is a perspective view of a compressible retention ring intended to be used with a lock as shown in FIGS. 2 and 3;

DESCRIPTION OF THE PREFERRED EMBODIMENTS

Figure 1:
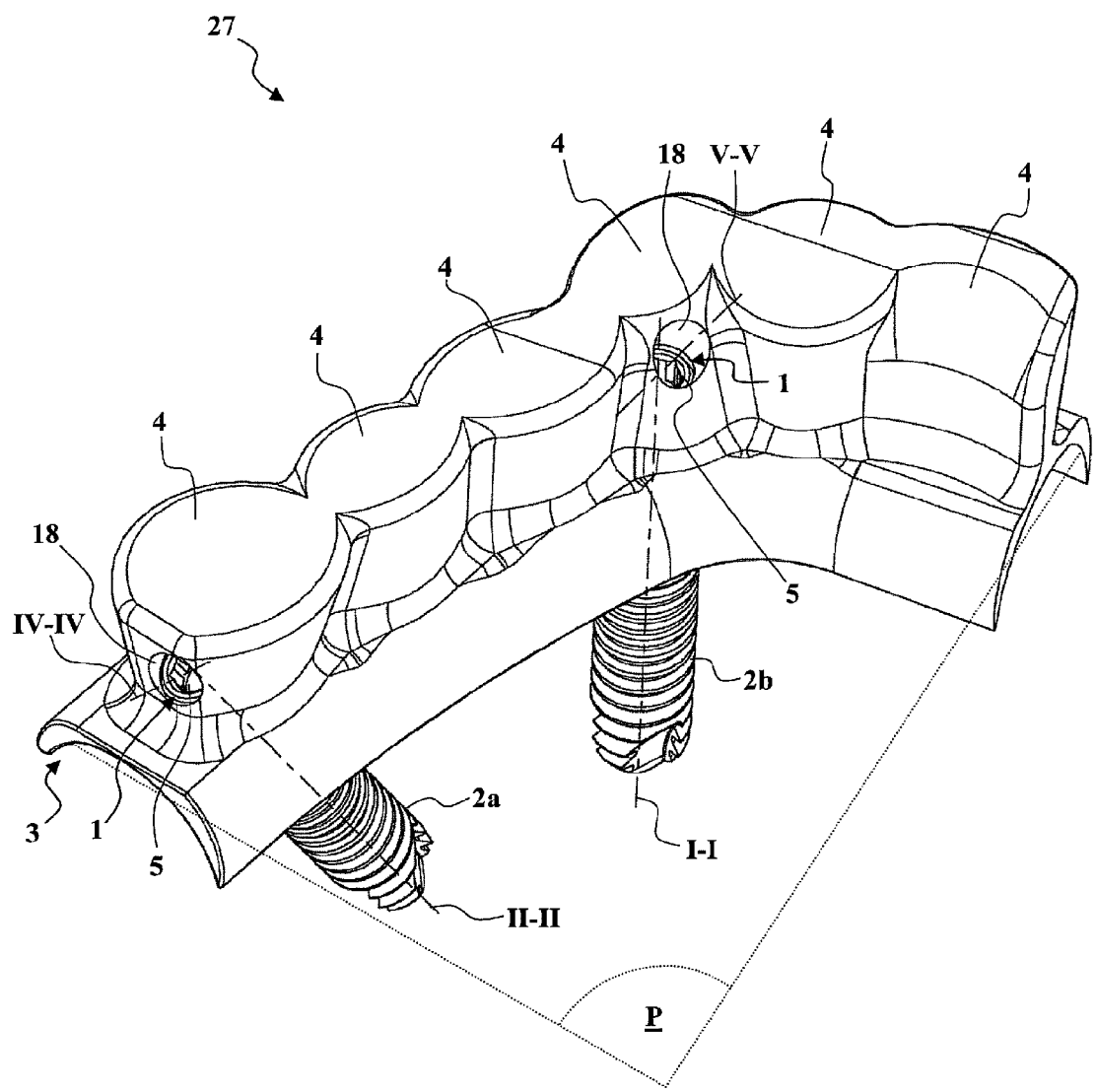
FIG. 1 is a perspective view of part of a dental prosthesis transfixed on dental implants by connecting devices, this being representative of a first embodiment of a dental prosthetic assembly according to the invention.

FIGS. 1 to 8 illustrate a first embodiment of a dental prosthetic assembly 27 according to the invention, comprising dental implants 2a and 2b and a transfixed dental prosthesis 3. The dental prosthesis 3 here is a multiple prosthesis (that is to say permitting the restoration of several teeth 4) which is supported on a plurality of dental implants 2a and 2b. For greater clarity, only half of the dental prosthesis 3 has been shown, the other half being substantially symmetrical to that shown in FIG. 1. The dental prosthesis 3 thus has the general shape of an arc and is intended to rest on four dental implants (two per half of the dental prosthesis 3). It is possible, however, to use a greater or smaller number of dental implants.

As is illustrated in FIG. 1, the dental prosthesis 3 is intended to rest on a substantially plane surface P corresponding to the general surface of the dental arch of the patient.

The dental implant more specifically designated by reference sign 2a has a direction of extent II-II determining its axial direction of screwing into the jaw of the patient. The dental implant 2a is screwed into the anterior part of the jaw of the patient.

Similarly, the dental implant more specifically designated by reference sign 2b has a direction of extent I-I defining its direction of screwing into the posterior part of the jaw of the patient.

In the example illustrated in FIG. 1, it will be noted that the axial direction I-I is substantially perpendicular to the substantially plane surface P, whereas the axial direction II-II is oblique with respect to the substantially plane surface P. The oblique implantation of the dental implant 2a in the jaw of the patient allows it to engage in an area of bone that has better solidity, so as to guarantee satisfactory stability of the dental prosthesis 3. The implantations in non-parallel directions I-I and II-II increase the resistance of all the implants so as to withstand the stresses applied to the dental prosthesis 3 during its use.

In order to fix the dental prosthesis 3 on the dental implants 2a and 2b, use is made of connecting devices 1 which each comprise a lock 5 illustrated more particularly in FIGS. 2 and 3. In these figures, it will be seen that the lock 5 has three radial wings 6a to 6c and extends longitudinally in an axial direction III-III.

Each lock 5 is mounted in the dental prosthesis 3 by means of a compressible retention ring 7 as illustrated in FIG. 4. The retention ring 7 is provided with a substantially radial slit 8 allowing it to be clipped onto the lock 5. In the case in point, the retention ring 7 is mounted in an outer peripheral groove 9 formed on the lock 5.

Figure 5:
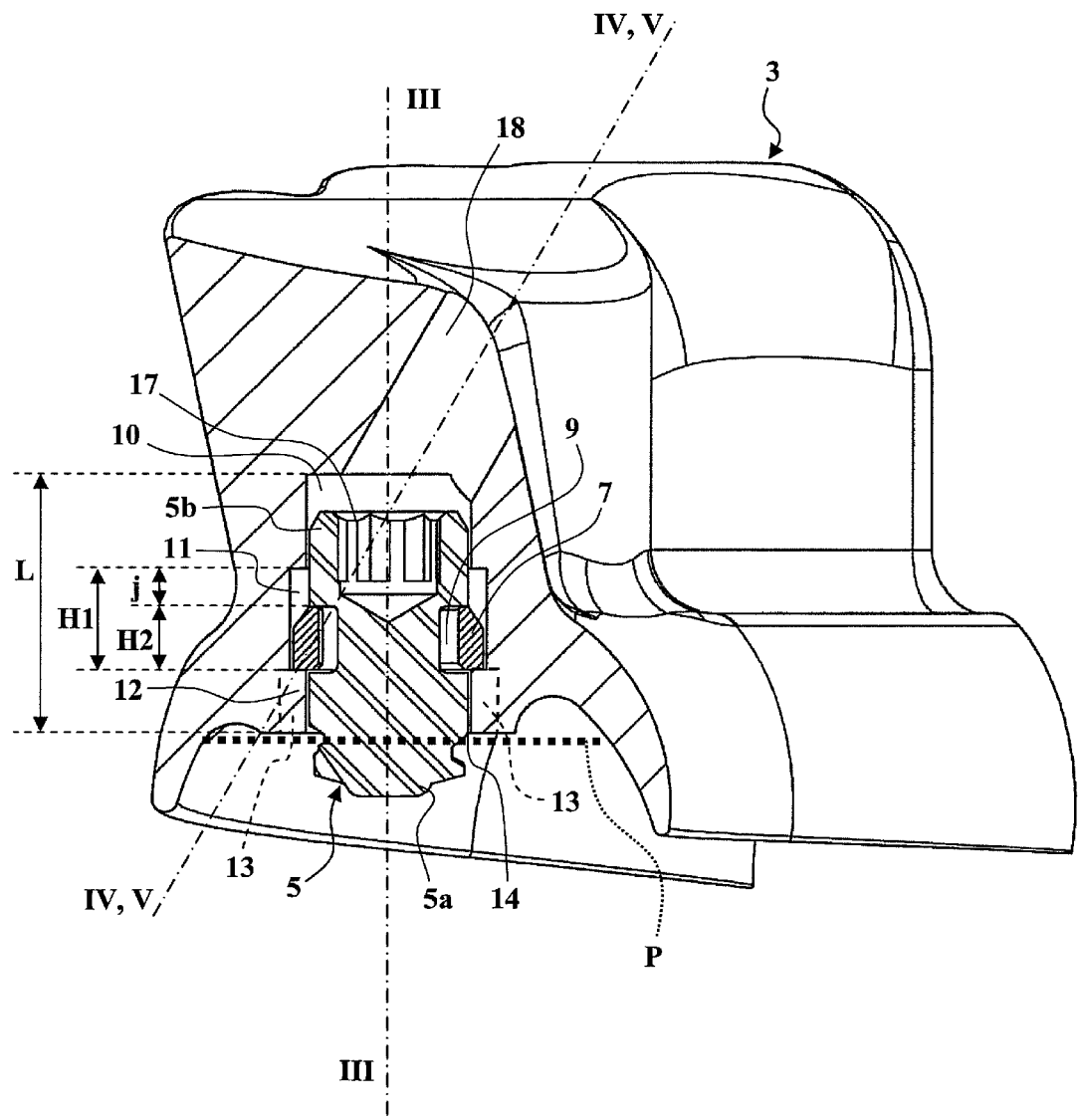
FIG. 5 is a sectional view of the dental prosthesis illustrated in FIG. 1.

As is illustrated in FIG. 5, the lock 5 is intended to be mounted rotatably and to be retained in translation in the dental prosthesis 3 in a receiving seat 10. The receiving seat 10 has an inner peripheral groove 11.

In its lower part, the receiving seat 10 has an annular shoulder 12, such that the receiving seat 10 has, in its lower part, a lower orifice 14 of smaller cross section than the external diameter of the retention ring 7. By virtue of its being compressible, the retention ring 7 can decrease in external diameter in order to penetrate into the lower orifice 14 and pass the shoulder 12 to more closely enclose the bottom of the outer peripheral groove 9. Once the lock 5, provided with its retention ring 7, has been inserted axially into the receiving seat 10, the retention ring 7 expands radially and simultaneously engages in the outer peripheral groove 9 and in the inner peripheral groove 11. The lock 5 is thus held captive in the dental prosthesis 3.

If the lock 5 is damaged, it may be necessary to remove it from the receiving seat 10 without damaging the dental prosthesis 3.

To do this, axial channels 13, illustrated by broken lines in FIG. 5, are provided, which extend from the lower orifice 14 of the receiving seat 10 as far as the inner peripheral groove 11. A tool for removing the retention ring 7 can thus be placed around the retention ring 7 in order to compress the latter and reduce its external diameter in order to withdraw it via the lower orifice 14.

Figure 6:
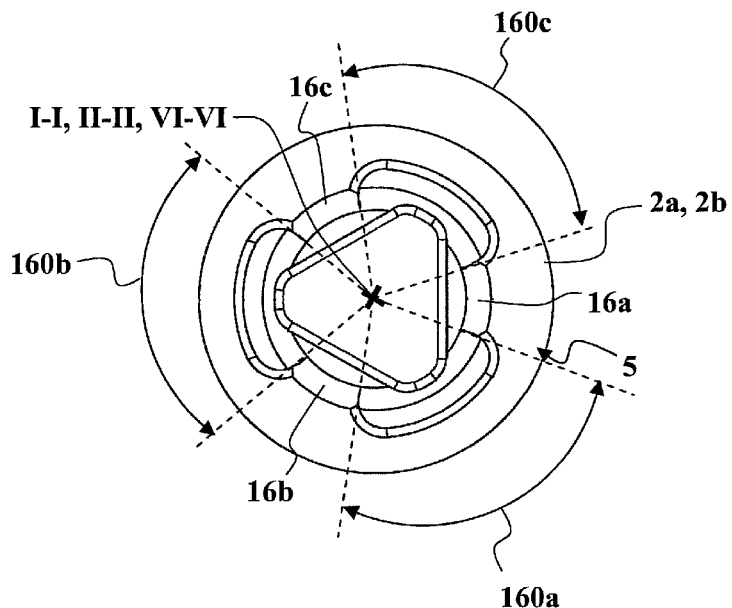
FIG. 6 is a plan view of an implant to which the dental prosthesis illustrated in FIG. 5 is intended to be attached.
Figure 7:
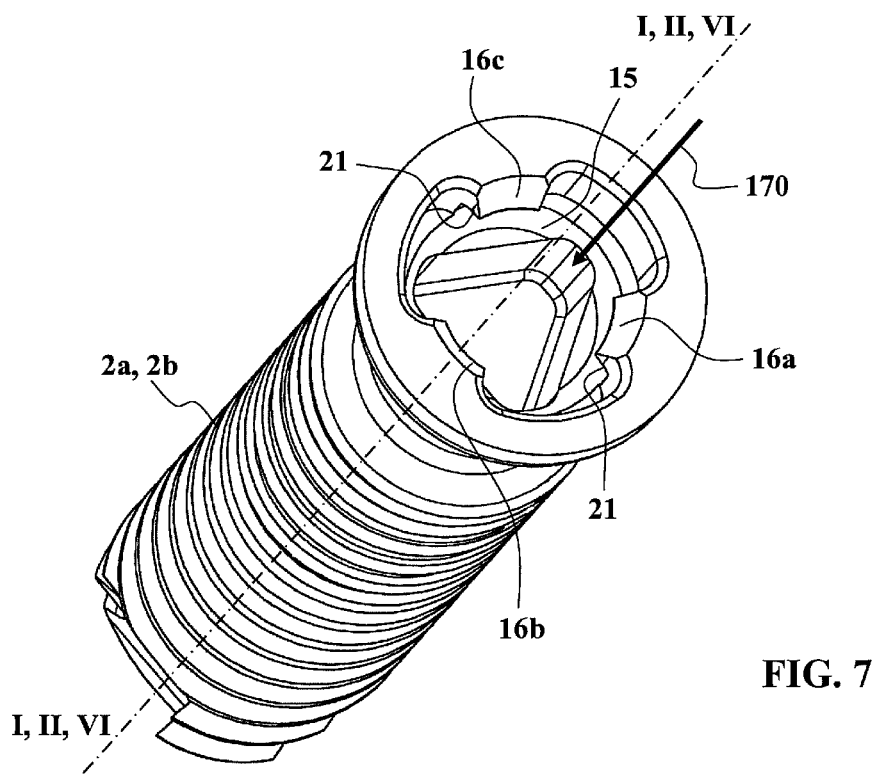
FIG. 7 is a perspective view of the implant from FIG. 6.
Figure 8:
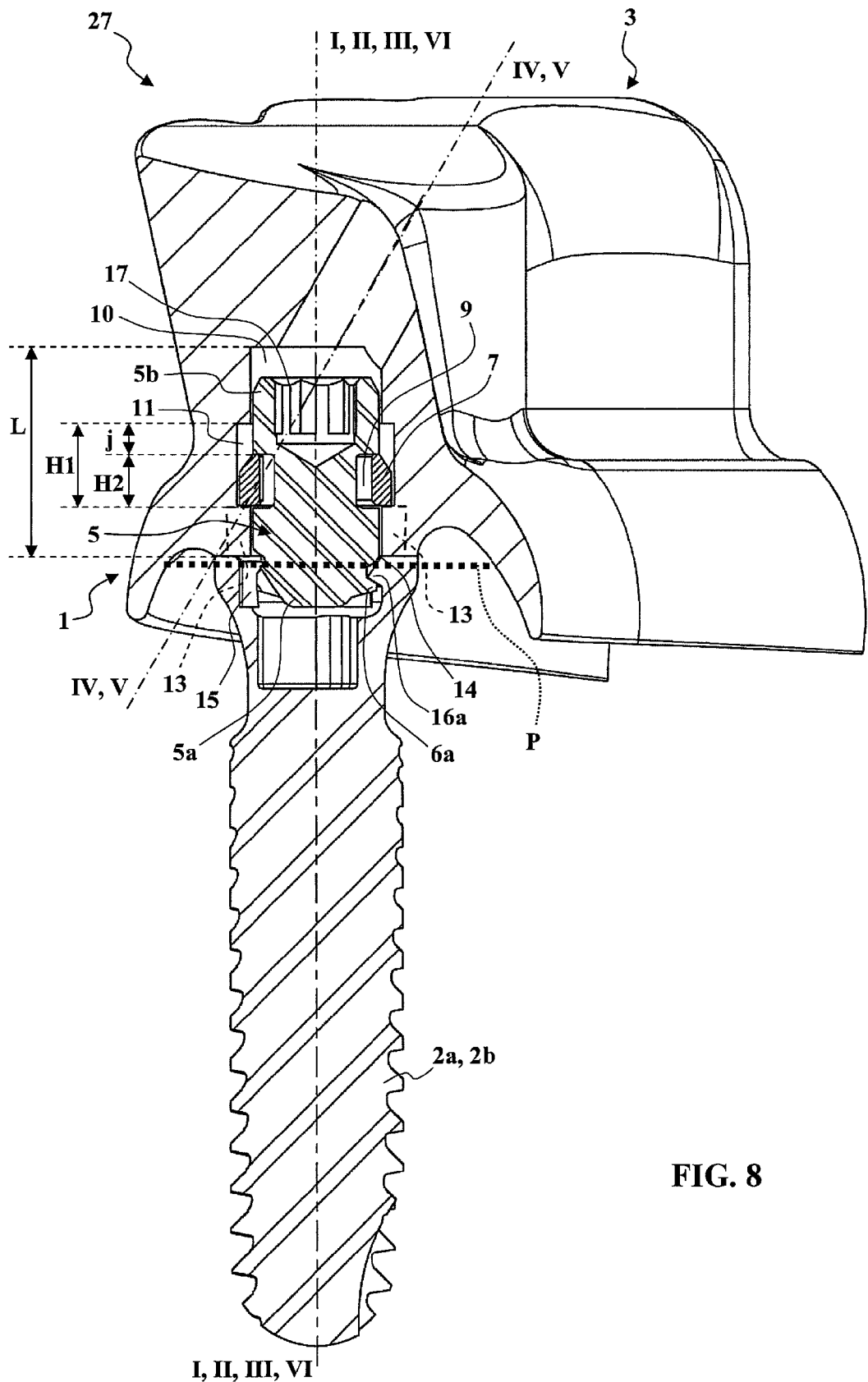
FIG. 8 is a sectional view illustrating the cooperation between the dental prosthesis illustrated in FIG. 5 and the implant illustrated in FIGS. 6 and 7.
Figure 9:
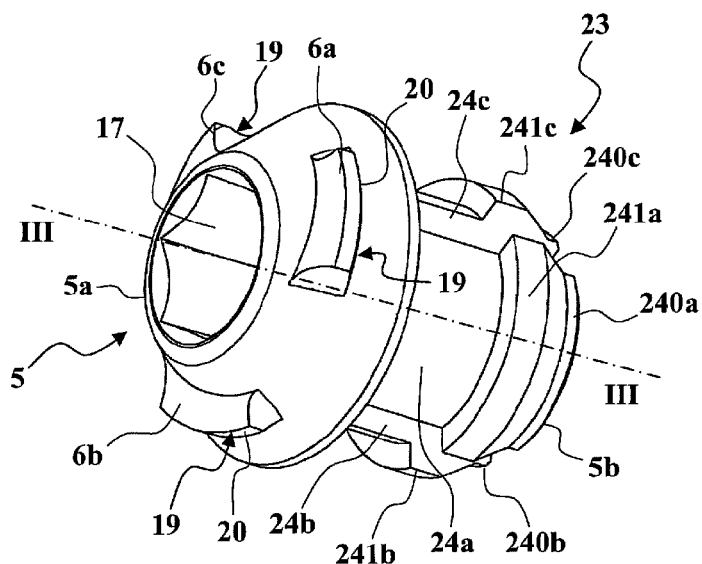
FIG. 9 is a perspective view of a lock used in a dental prosthetic assembly according to a second embodiment of the invention.
Figure 10:
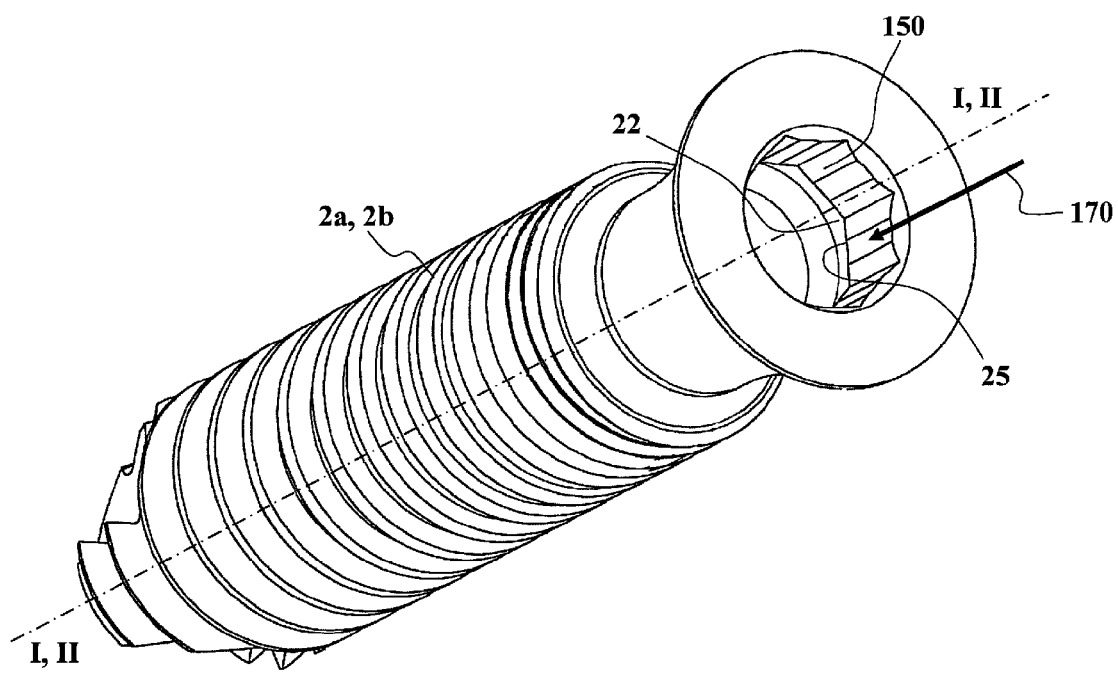
FIG. 10 is a perspective view of an implant intended to receive, at its upper end, the lock illustrated in FIG. 9.
Figure 11:
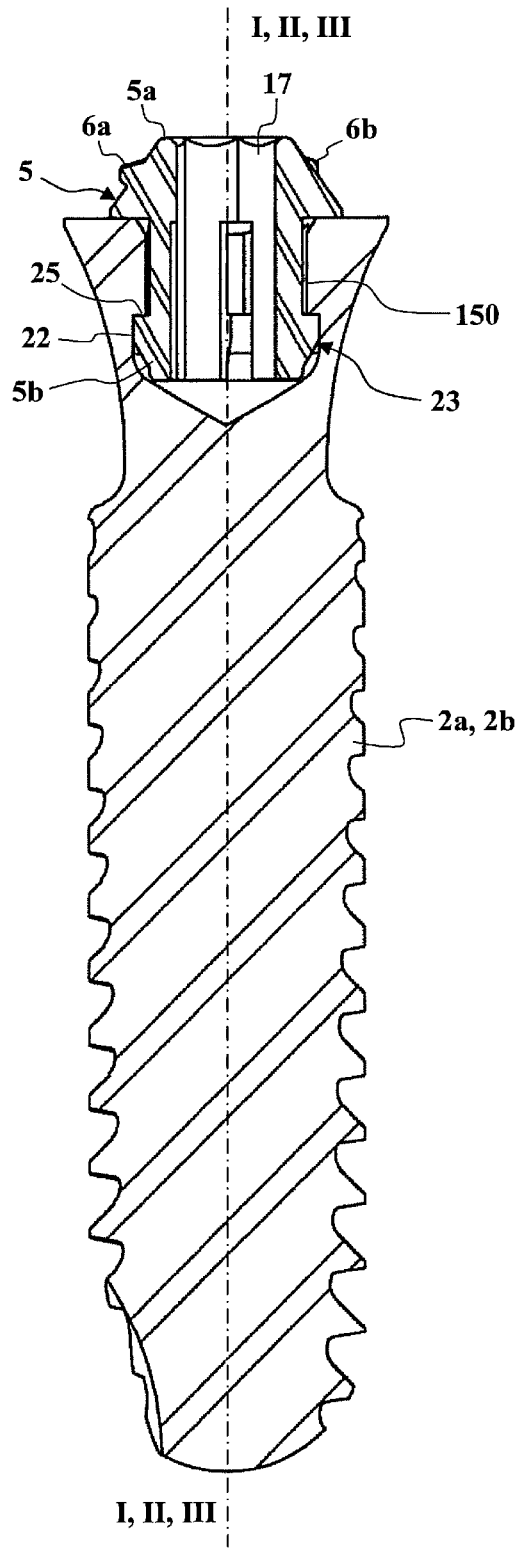
FIG. 11 is a sectional view of the implant from FIG. 10, provided with a lock such as that illustrated in FIG. 9.

The lock 5 is intended to cooperate directly with a dental implant 2a or 2b of the kind illustrated in FIGS. 6 and 7. In these figures, it will be seen that the implant 2a or 2b has a retention cavity 15 with three protuberances 16a to 16c extending radially towards the centre of the retention cavity 15.

The radial wings 6a to 6c and the protuberances 16a to 16c are configured and dimensioned in such a way as to cooperate by rotation of the lock 5 in order to keep the dental prosthesis 3 transfixed on the dental implant 2. Moreover, the radial wings 6a to 6c and the protuberances 16a to 16c are configured dimensionally to allow penetration of the lock 5 and of its radial wings 6a to 6c into the retention cavity 15 by a simple movement of axial translation, illustrated by the arrow 170 in FIG. 7.

To do this, the radial wings 6a to 6c of the lock 5 are separated from each other by angular sectors 60a to 60c, which are dimensioned to allow a protuberance 16a, 16b or 16c to pass during the movement of axial translation 170. Moreover, the protuberances 16a to 16c of the retention cavity 15 are separated from each other by angular sectors 160a to 160c, which are dimensioned to allow a radial wing 6a, 6b or 6c to pass during the simple movement of axial translation 170. In the example illustrated in FIGS. 3 and 6, the angular sectors 60a to 60c extend angularly through 70°, with the radial wings 6a to 6c extending angularly through 50°. For their part, the angular sectors 160a to 160c extend angularly through 80°, while the protuberances 16a to 16c extend angularly through 40°.

It will be seen more particularly from FIG. 2 that the radial wings 6a to 6c of the lock 5 are formed on a substantially frustoconical first end portion 5a. This truncated cone shape of the first end 5a permits relative centring between the lock 5 and the retention cavity 15.

It will be seen more particularly from FIG. 5 that the lock 5 has, at a second end 5b, a socket 17 allowing the lock 5 to be driven in rotation about the axial direction III-III with the aid of a tool. In the case in point, the socket 17 is polygonal. However, the socket 17 could have any suitable non-circular cross-sectional shape.

The socket 17 can in particular be configured according to the teaching of document EP 2 607 722 A1 in order to allow the use of a rotation drive tool that permits a ball joint effect.

Alternatively or in addition, the rotation tool can be specifically adapted to drive the lock 5 in rotation by accessing the socket 17 via the access channel 18, which extends in an axial direction IV-IV or oblique direction V-V with respect to the axial direction III-III (FIG. 5) and oblique with respect to the substantially plane general support surface P of the dental prosthesis 3.

It will be seen more particularly from FIG. 2 that the radial wings 6a to 6c have a bearing facet 19 with a progressive incline 20 intended to bear against a protuberance 16a, 16b or 16c of the retention cavity 15. The progressive incline 20 of the radial wings 6a to 6c makes it possible to ensure good radial guidance and good axial pressing of the dental prosthesis 3 against the implant 2.

Alternatively or in addition, the protuberances 16a to 16c can have a retention facet 21 with progressive incline intended to bear against a radial wing 6a to 6c of the lock 5.

To produce the dental prosthesis 3 intended to be fixed to the dental implants 2a and 2b previously implanted in the jaw of the patient, the prosthetist uses an impression that was taken by the dentist and that identifies the directions I-I and II-II in which the implants 2a and 2b are oriented. In this way, the prosthetist can envisage orienting the locks 5 with respect to the dental prosthesis 3 in such a way as to cause the axial directions of extent III-III of the locks 5 to coincide with the axial directions I-I and II-II, while orienting the access channels 18 in the respective directions IV-IV and V-V in order to provide access to the locks 5 and to allow the locks 5 to be driven in rotation about the axial directions III-III by means of a rotation drive tool that permits a ball joint effect. The ball joint effect permits a considerable freedom of choice of the angles between the axial directions I-I and V-V on the one hand and II-II and IV-IV on the other hand. The prosthetist can thus place the access channels 18 such that they do not open out on an active surface area of the teeth that is intended to withstand considerable mastication forces.

Once the dental prosthesis 3 has been produced by the prosthetist, it is sent to the dentist in order to be fixed in the patient's mouth on the dental implants 2a and 2b.

To do this, the dentist starts by positioning the dental prosthesis 3 on the dental arch of the patient in order to check that the dental prosthesis 3 is a good fit for the oral cavity.

During this positioning phase, the locks 5 are situated with their longitudinal direction III-III coaxial to the axial directions I-I and II-II.

If the radial wings 6a to 6c are situated in line with the angular sectors 160a to 160c, the lock 5 and its radial wings 6a to 6c penetrate into the retention cavity 15 by a simple movement of axial translation during the positioning of the dental prosthesis 3 on the dental arch of the patient. The dental prosthesis 3 can thus bear satisfactorily along the entire length of the dental arch of the patient.

Once the positioning has been carried out and checks have been made, the dentist rotates the locks 5 by way of a rotation drive tool, which he inserts into the access channels 18 in the axial directions IV-IV and V-V. The rotation drive tool is configured in such a way as to allow the lock 5 to be driven in rotation with a ball joint effect as described, for example, in the document EP 2 607 722 A1.

While the locks 5 are driven in rotation, the radial wings 6a to 6c come to bear with their bearing facets 19 against the retention facets 21 of the protuberances 16a to 16c, and the progressive inclines 20 of the bearing facets 19 are able to press the dental prosthesis 3 onto the dental implants 2a and 2b. This leads to the position illustrated in FIG. 8.

However, it is possible that, during the positioning of the dental prosthesis 3 on the dental arch of the patient, the radial wings 6a to 6c are at least partially in line with the protuberances 16a to 16c. In this case, in order to ensure that the locks 5 do not prevent the dental prosthesis 3 from being pressed correctly onto the dental arch of the patient, provision is made that the inner peripheral groove 11 has a height H1 slightly greater than the height H2 of the retention ring 7. This difference between the heights H1 and H2 induces an axial play j in translation between the dental prosthesis 3 and the locks 5. In practice, the axial play j and the length L of the receiving seat 10 are dimensioned in such a way as to permit a movement of the lock 5 in the dental prosthesis 3 in order to ensure that the lock 5 does not prevent satisfactory positioning of the dental prosthesis 3 on the dental arch of the patient. The play j and the length L are also dimensioned such that the rotation drive tool can still effectively drive the lock 5 in rotation about the axial direction by being inserted into the access channel 18 oriented in the axial direction IV-IV, despite the retreat of the lock 5.

FIGS. 9 to 15 illustrate a dental prosthetic assembly 27 according to a second embodiment of the invention.

In this second embodiment, the lock 5 is mounted rotatably and captive on the dental implant 2a or 2b. To do this, the dental implant 2a or 2b has an inner peripheral groove 22 of circular cross section, situated in the inner part of the receiving cavity 150 formed in the dental implant 2a or 2b. As can be seen more particularly from FIGS. 9 and 11, the lock 5 for its part has, at its second end 5b, snap-fit means 23 intended to penetrate into the inner peripheral groove 22 of the receiving cavity 150. In the case in point, the snap-fit means 23 have three wings 24a to 24c with free ends 240a to 240c having elastic radial movement. The free ends 240a to 240c are also provided with ribs 241a to 241c intended to snap-fit into the inner peripheral groove 22 and to be retained there by a shoulder 25 situated above the inner peripheral groove 22.

The polygonal socket 17, allowing the lock 5 to be driven in rotation, passes longitudinally through the length of the lock 5 in the axial direction thereof and thus opens out at the first end 5a of the lock 5.

Figure 12:
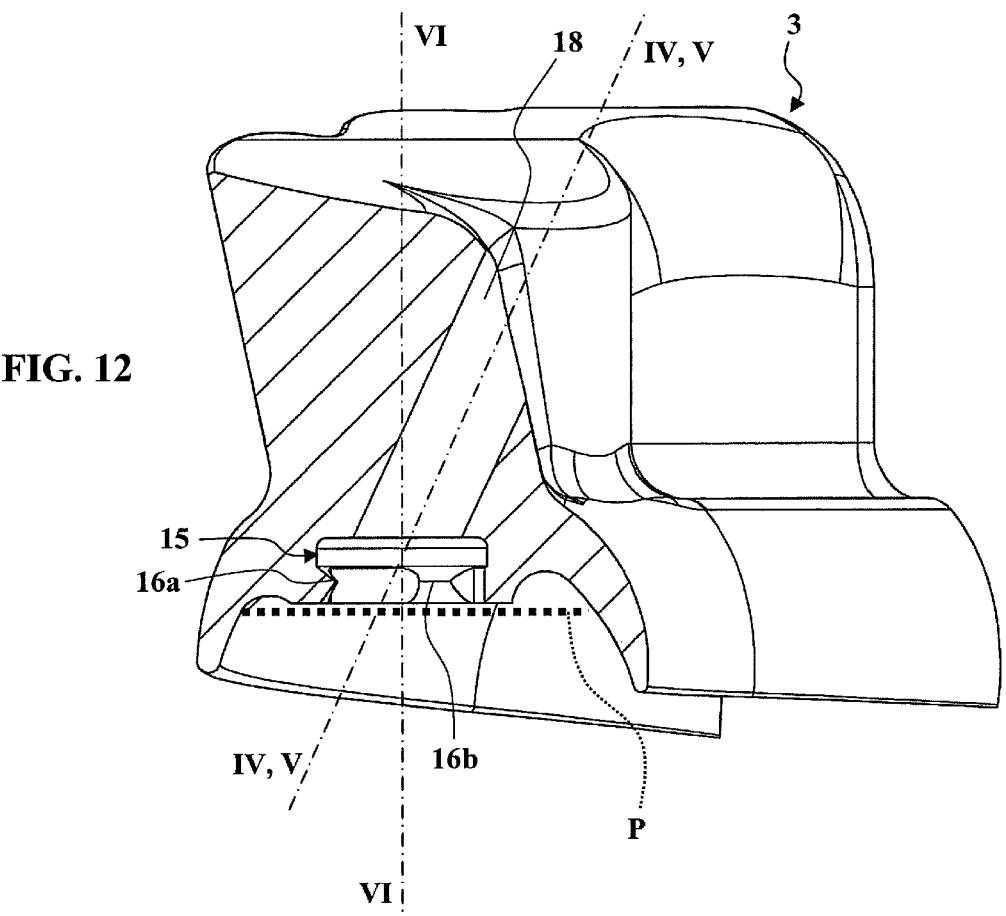
FIG. 12 is a sectional view of a dental prosthesis intended to be retained on the implant from FIG. 11.
Figure 13:
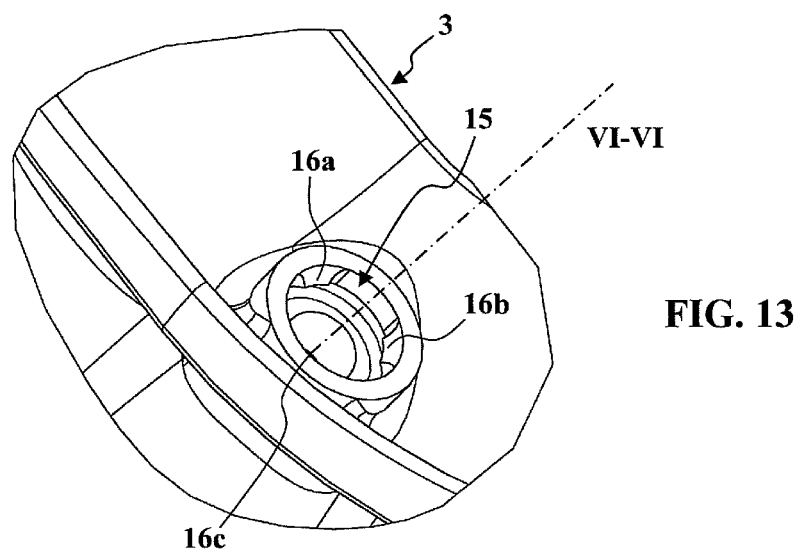
FIG. 13 is a perspective view of a retention cavity provided in the dental prosthesis illustrated in FIG. 12.
Figure 14:
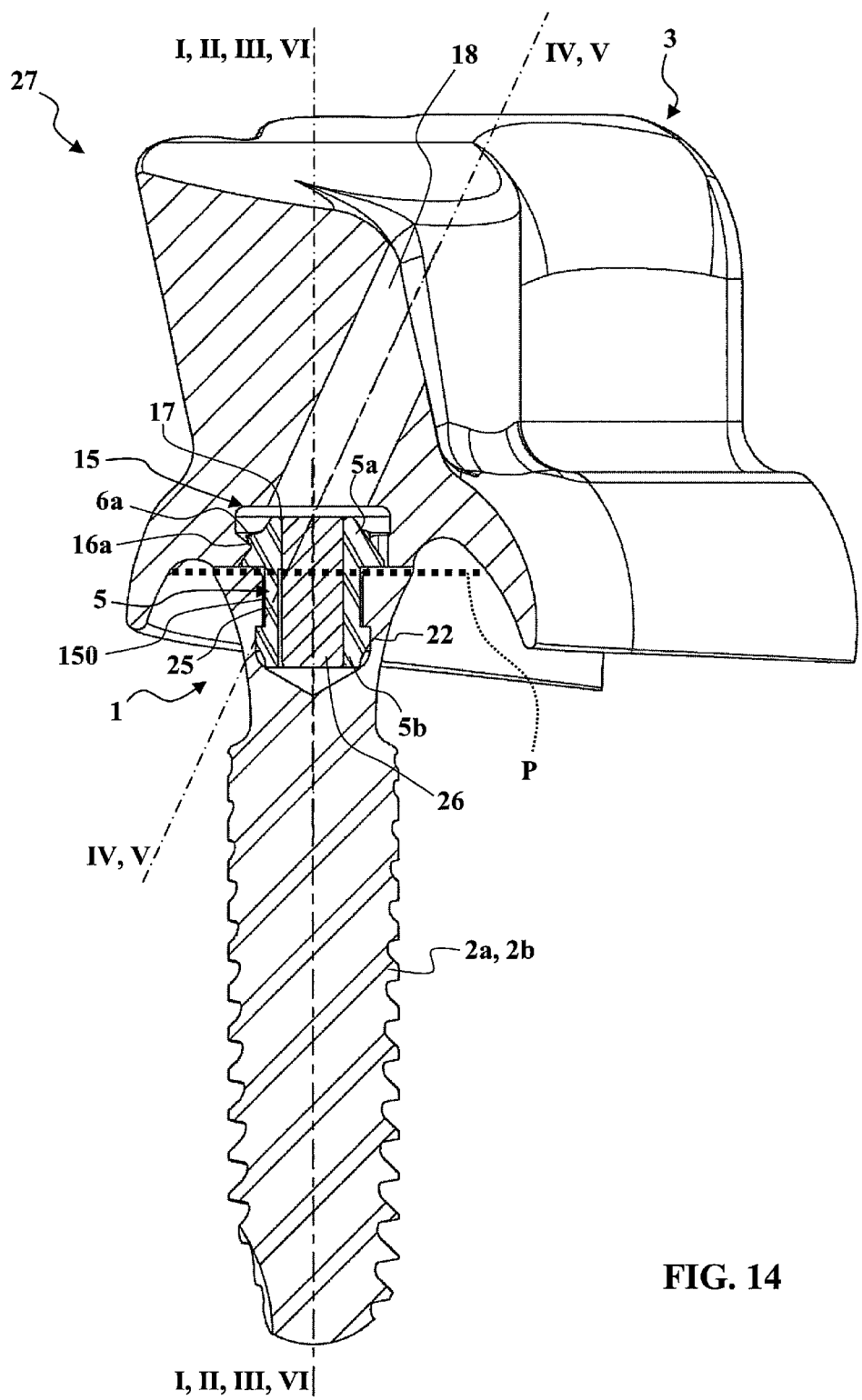
FIG. 14 is a sectional view illustrating the cooperation between the dental prosthesis illustrated in FIG. 12 and the implant illustrated in FIG. 11.

For its part, the dental prosthesis 3 is provided with the retention cavity 15, as is illustrated in FIGS. 12 to 14.

The radial wings 6a to 6c and the protuberances 16a to 16c are configured similarly to what has been explained in connection with the first embodiment of the invention illustrated in FIGS. 1 to 8.

The connecting device 1 used in the second embodiment of the invention is similar to what has been explained in connection with the first embodiment of the invention, except that here it is the retention cavity 15 that is formed in the dental prosthesis 3 in such a way as to be oriented in the mouth of the patient in an axial direction VI-VI coaxial with respect to the axial directions I-I or II-II of the dental implants 2a and 2b. For its part, the lock 5 is arranged with its longitudinal direction coinciding with the axial direction I-I or II-II of the dental implants 2a and 2b.

During the fixation of the dental prosthesis 3 on the dental implants 2a and 2b, the dentist attaches locks 5 to the upper part of the implants 2a and 2b by snap-fit engagement. The dentist then positions the dental prosthesis 3 on the dental arch of the patient. This positioning is perfect if the radial wings 6a to 6c are not in line with the protuberances 16a to 16c. If this is not the case, the dentist drives the locks 5 slightly in rotation with the aid of a rotation drive tool that is inserted into the access channels 18, in order to arrange the radial wings 6a to 6c in line with the angular sectors 160a to 160c.

If the positioning proves satisfactory, the dentist then drives the locks 5 in rotation about their longitudinal direction so as to cause the bearing facets 19 of the radial wings 6a to 6c to cooperate with the retention facets 21 of the protuberances 16a to 16c. To do this, the dentist introduces a rotation drive tool into the socket 17 by passing it through the access channel 18 and through the retention cavity 15.

Figure 15:
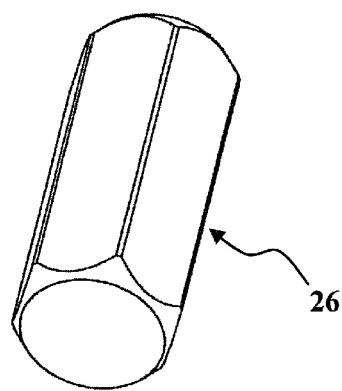
FIG. 15 is a perspective view of a blocking component.

In order to guarantee that the locks 5 remain permanently on the dental implants 2a and 2b, the dentist inserts into the socket 17 the blocking component 26 illustrated in FIG. 15, which blocking component 26 has an external shape matching the internal shape of the socket 17. The blocking component 26 has dimensions allowing it to be inserted with slight force into the socket 17 of the lock 5. Once in place, as illustrated in FIG. 14, the blocking component 26 prevents any centripetal radial flexion of the elastic wings 24a to 24c, such that the ribs 241a to 241c remain correctly in position in the inner peripheral groove 22 situated in the receiving cavity 150 formed in the dental implant 2a and 2b.

This leads to the position illustrated in FIG. 14.

Although the above description has been given in relation to an implant-supported multiple prosthesis of the transfixed type, that is to say fixed to several implants in the jaw of the patient, the invention can also be used for a single implant-supported prosthesis of the transfixed type, that is to say fixed to just one implant in the jaw of the patient.

However, the connecting device according to the invention has important additional advantages in the case of a dental prosthetic assembly 27 comprising a transfixed multiple dental prosthesis 3 supported on a plurality of dental implants 2a and 2b, especially during the phase of positioning of the dental prosthesis 3 on the dental arch of the patient.

The transfixed multiple dental prosthesis 3 supported on implants can include a connecting bar intended to mechanically interconnect the dental implants on which the dental prosthesis 3 is to be fixed. In the embodiments illustrated in the figures, the dental prosthesis 3 has no connecting bar.

The present invention is not limited to the embodiments that have been explicitly described, and instead it includes the variants and generalizations contained within the scope of the attached claims.

The invention claimed is:

1. A dental prosthetic assembly comprising:
   a dental implant,
   a dental prosthesis,
   a connecting device comprising a retention cavity, which is formed in one of dental implant or dental prosthesis and which is provided on its periphery with protuberances extending radially towards the centre of the retention cavity,
wherein:
   the dental prosthesis is of the transfixed type,
   the connecting device comprises a lock which has at least two radial wings and is mounted rotatably and retained in translation in the other of dental implant or dental prosthesis, the radial wings and the protuberances being configured and dimensioned in such a way as to allow the lock and its radial wings to penetrate into the retention cavity by a simple movement of axial translation,
   the radial wings and the protuberances are configured and dimensioned in such a way as to cooperate by rotation of the lock in order to keep the dental prosthesis transfixed on the dental implant.

2. The dental prosthetic assembly according to claim 1, wherein:
   the radial wings of the lock are separated from each other by angular sectors which are dimensioned in such a way as to allow a protuberance to pass through by a simple movement of axial translation,
   the protuberances of the retention cavity are separated from each other by angular sectors which are dimensioned in such a way as to allow a radial wing to pass through during said simple movement of axial translation.

3. The dental prosthetic assembly according to claim 1, wherein the radial wings of the lock are carried by a first end portion, which is substantially conical or frustoconical.

4. The dental prosthetic assembly according to claim 1, wherein the lock has a socket allowing it to be driven in rotation with the aid of a tool.

5. The dental prosthetic assembly according to claim 1, wherein the radial wings have a bearing facet with a progressive incline intended to bear against a protuberance of the retention cavity, and/or in that the protuberances have a retention facet with a progressive incline intended to bear against a radial wing of the lock.

6. The dental prosthetic assembly according to claim 1, wherein the lock is mounted rotatably and retained in translation in the dental prosthesis by way of a compressible retention ring, preferably by means of a slit, engaging simultaneously in an outer peripheral groove formed on the lock and in an inner peripheral groove formed in the dental prosthesis.

7. The dental prosthetic assembly according to claim 6, wherein the dental prosthesis has a plurality of open axial channels extending as far as the inner peripheral groove formed in the dental prosthesis.

8. The dental prosthetic assembly according to claim 6, wherein the inner peripheral groove, formed in the dental prosthesis, and/or the outer peripheral groove, formed on the lock, have a height which is slightly greater than that of the retention ring, permitting axial play in translation between the dental prosthesis and the lock.

9. The dental prosthetic assembly according to claim 1, wherein the lock is mounted rotatably and retained in translation in the dental implant by way of:
   an inner peripheral groove situated in a receiving cavity formed in the dental implant,
   a second end of the lock having snap-fit means intended to penetrate into the inner peripheral groove of the receiving cavity.

10. The dental prosthetic assembly according to claim 1, wherein:
    it comprises a plurality of dental implants,
    the transfixed dental prosthesis is an implant-supported multiple prosthesis.

11. The dental prosthetic assembly according to claim 1, wherein the dental prosthesis comprises at least one access channel oriented in a direction oblique with respect to the substantially plane general bearing surface of the dental prosthesis.

\* \* \* \* \*